United States Patent
Carson et al.

(10) Patent No.: US 12,394,527 B2
(45) Date of Patent: Aug. 19, 2025

(54) SYSTEMS AND METHODS FOR DETECTING EATING PATTERNS OF A PET

(71) Applicant: Mars, Incorporated, McLean, VA (US)

(72) Inventors: Aletha Carson, Gaston, OR (US);
David Allen, Charleston, SC (US);
Laura Prescott, Makawao, HI (US)

(73) Assignee: Mars, Incorporated, McLean, VA (US)

( * ) Notice: Subject to any disclaimer, the term of this patent is extended or adjusted under 35 U.S.C. 154(b) by 6 days.

(21) Appl. No.: 18/062,238

(22) Filed: Dec. 6, 2022

(65) Prior Publication Data
US 2023/0178246 A1 Jun. 8, 2023

Related U.S. Application Data

(60) Provisional application No. 63/286,721, filed on Dec. 7, 2021.

(51) Int. Cl.
*G16H 50/30* (2018.01)
*A61B 5/00* (2006.01)
*G16H 50/70* (2018.01)

(52) U.S. Cl.
CPC ........... *G16H 50/30* (2018.01); *A61B 5/6802* (2013.01); *G16H 50/70* (2018.01); *A61B 2503/40* (2013.01)

(58) Field of Classification Search
CPC ...... G16H 50/30; G16H 50/70; A61B 5/6802; A61B 2503/40
See application file for complete search history.

(56) References Cited

U.S. PATENT DOCUMENTS

2001/0011527 A1    8/2001 Ulman et al.
2008/0186166 A1*   8/2008 Zhou .................... G01S 5/0027
                                                340/506

(Continued)

FOREIGN PATENT DOCUMENTS

EP             3264299 A1  *  1/2018
WO       WO-2014118788 A2  *  8/2014  ........... A01K 29/005
WO          2015022608 A1     2/2015

OTHER PUBLICATIONS

"No Sensor Data," Sep. 17, 2021, https://web.archive.org/web/20210917132619/http://autosleep.tantsissa.com/wtdnosensordata (Year: 2021).*

(Continued)

*Primary Examiner* — Sun M Li
(74) *Attorney, Agent, or Firm* — Bookoff McAndrews, PLLC

(57) ABSTRACT

A computer-implemented method for using historical pet eating data to determine changes in pet eating behavior is disclosed. The method includes receiving a plurality of historical pet eating data records from a database, determining a subset of the plurality of historical pet eating data records, determining an expected distribution based on the subset of the plurality of historical pet eating data records wherein the expected distribution includes a baseline, an upper threshold, and a lower threshold, receiving current pet data from a pet sensor wherein the current pet data includes a total meal event value, analyzing whether the total meal event value exceeds the upper threshold or the lower threshold, and outputting a notification indicating a result that is responsive to the analyzing.

20 Claims, 25 Drawing Sheets

(56) References Cited

U.S. PATENT DOCUMENTS

| | | | |
|---|---|---|---|
| 2017/0095206 A1* | 4/2017 | Leib | A61B 5/14542 |
| 2017/0155674 A1* | 6/2017 | Seo | G06F 11/34 |
| 2019/0236465 A1* | 8/2019 | Vleugels | H04W 4/35 |
| 2019/0281370 A1* | 9/2019 | Struhsaker | H04W 4/80 |
| 2020/0305387 A1 | 10/2020 | Gibbs | |
| 2020/0381119 A1* | 12/2020 | Gibbs | G16H 40/67 |

OTHER PUBLICATIONS

Bell BM, Alam R, Alshurafa N, Thomaz E, Mondol AS, de la Haye K, Stankovix JA, Lach J, Spruijt-Metz D. Automatic wearable-based, in-field eating detection approaches for public health research: a scoping review. NPJ Digit Med. Mar. 13, 2020;3:38. doi: 10.1038/s41746-020-0246-2.PMID: 32195373; (Year: 2020).*

Chiou SY, Lin KJ, Dong YX. A Real-Time, Automatic, and Dynamic Scheduling and Control System for PET Patients Based on Wearable Sensors. Sensors (Basel). Feb. 5, 2021;21(4):1104. doi: 10/3990/s21041104. PMID: 33562605; PMCID: PMC7915651. (Year: 2021).*

J. M. Fontana, M. Farooq and E. Sazonov, "Automatic Ingestion Monitor: A Novel Wearable Device for Monitoring of Ingestive Behavior," in IEEE Transactions on Biomedical Engineering, vol. 61, No. 6, pp. 1772-1779, Jun. 2014, doi: 10.1109/TBME.2014.2306773 (Year: 2014).*

Nyein, H.Y.Y., Bariya, M., Tran, B. et al. A wearable patch for continuous analysis of thermoregulatory sweat at rest. Nat Commun 12, 1823 (2021). https://doi.org/10.1038/s41467-021-22109-z (Year: 2021).*

International Search Report issued in International Application No. PCT/US2022/080981 dated Mar. 14, 2023 (14 pages).

* cited by examiner

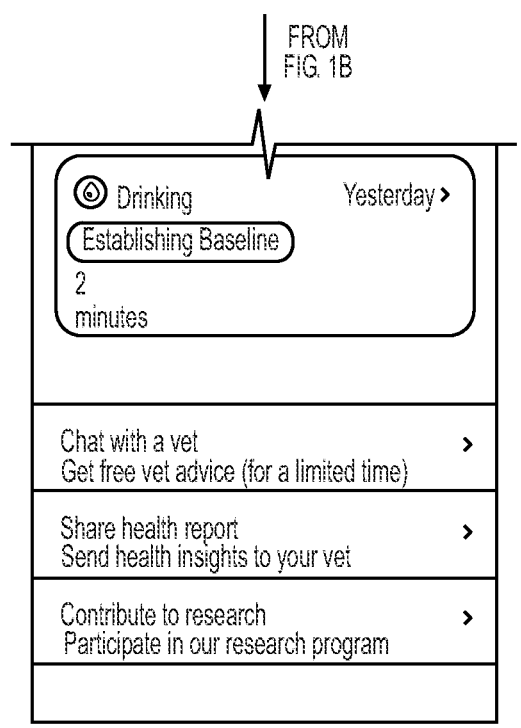
FIG. 1B (CONT. 1)

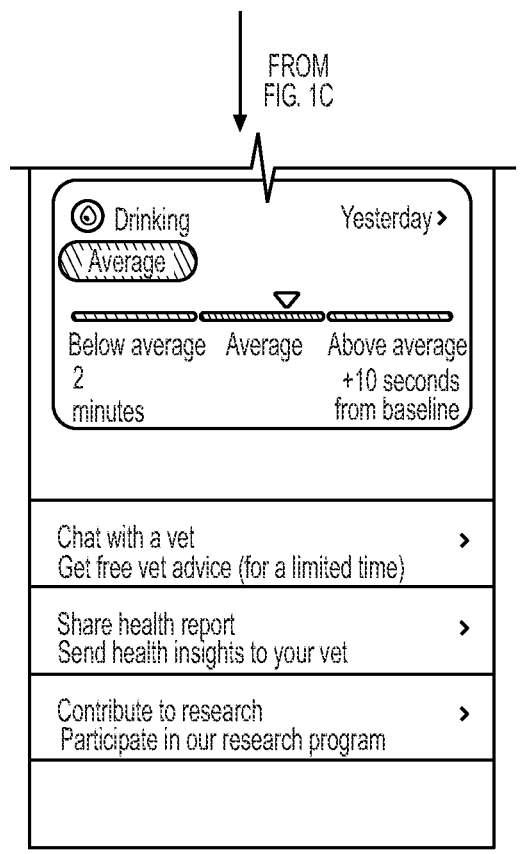
FIG. 1C (CONT. 1)

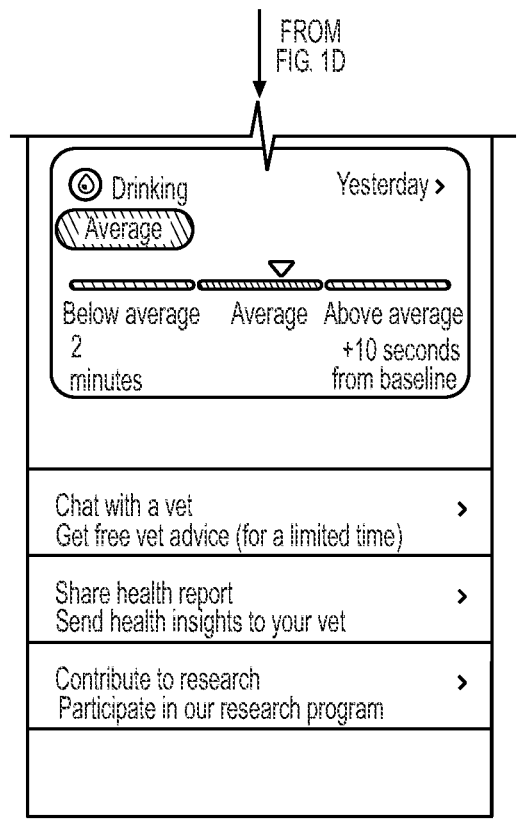
FIG. 1D (CONT. 1)

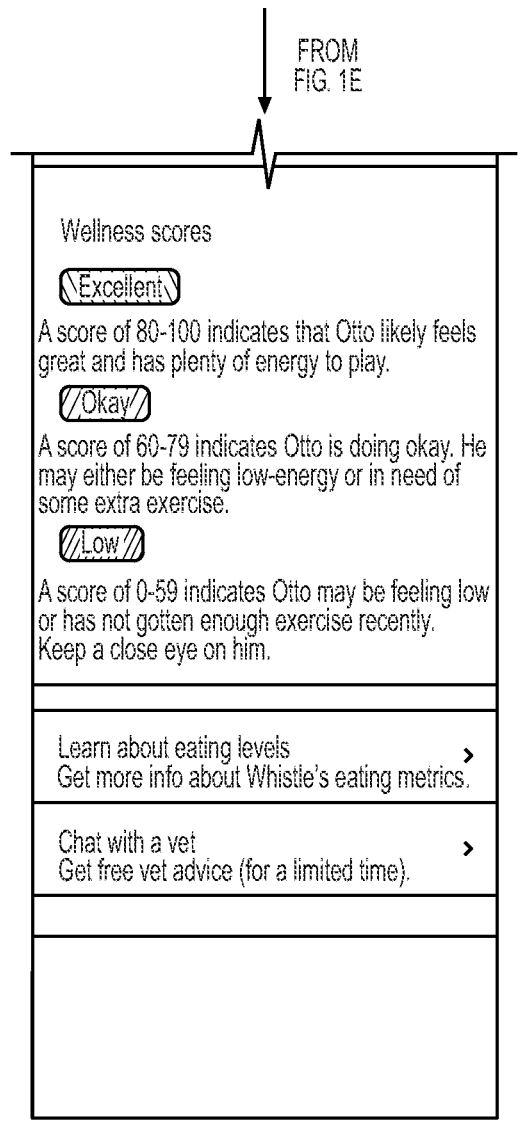
FIG. 1E (CONT. 1)

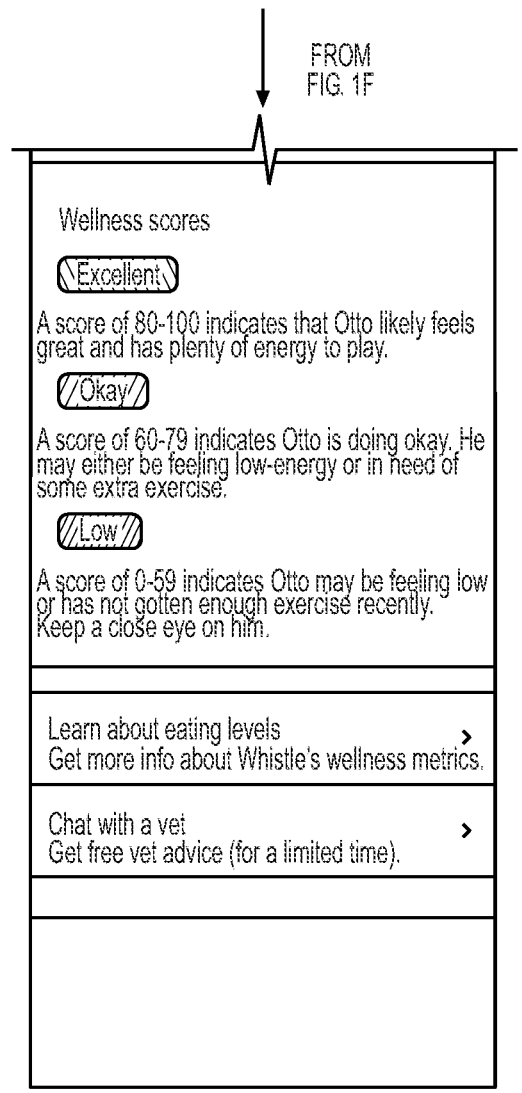
FIG. 1F (CONT. 1)

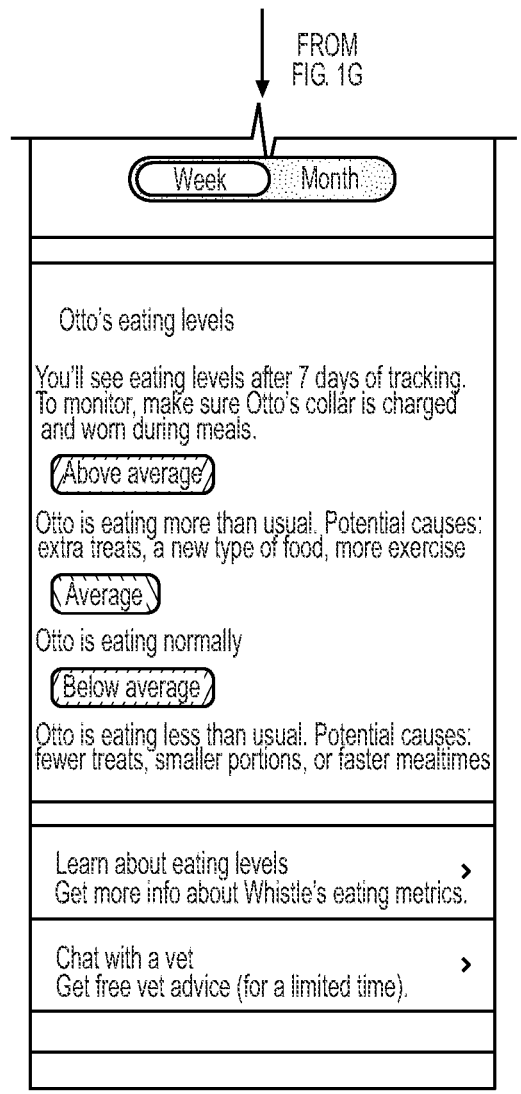
FIG. 1G (CONT. 1)

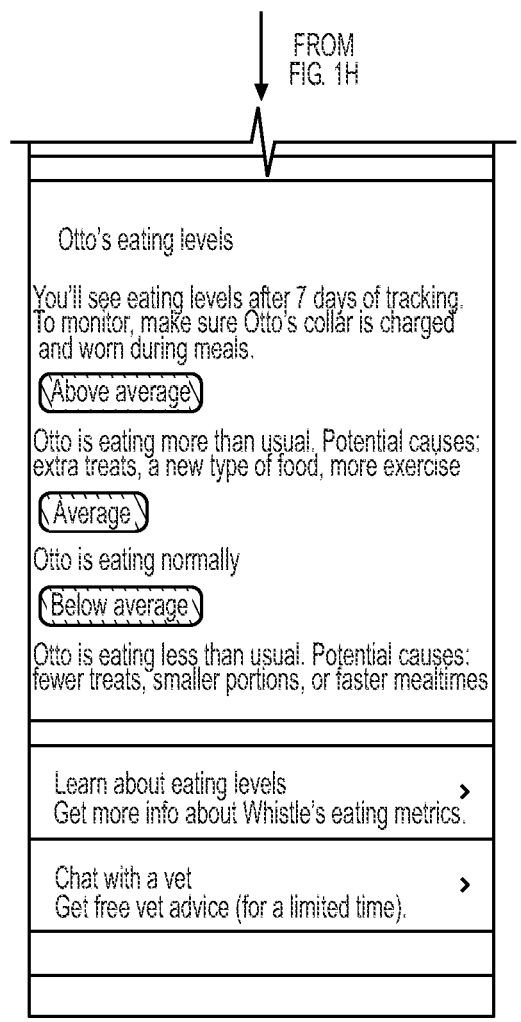
FIG. 1H (CONT. 1)

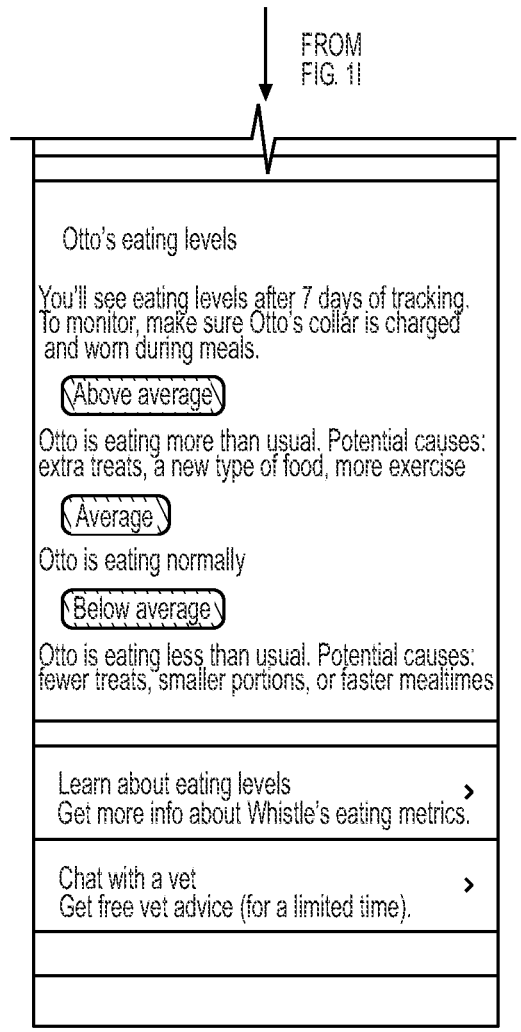
FIG. 1I (CONT. 1)

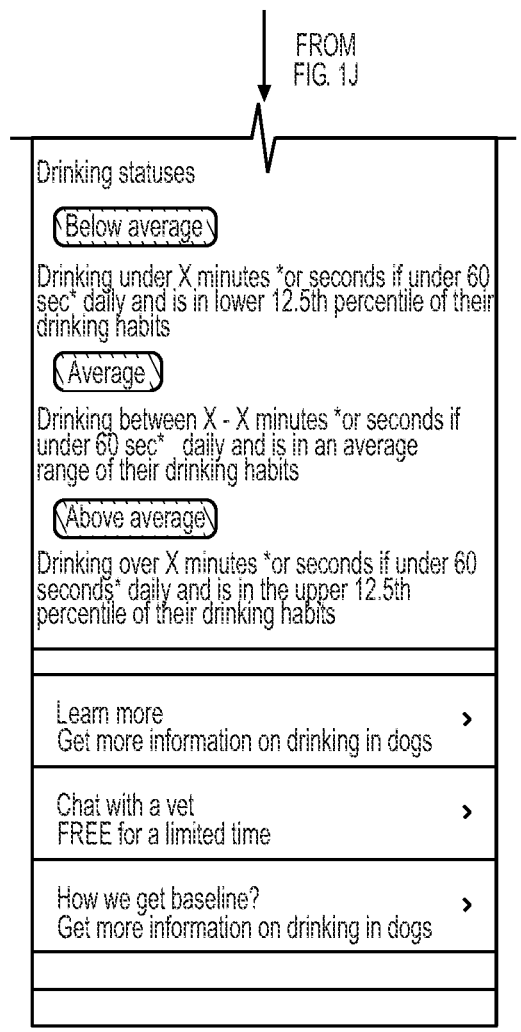
FIG. 1J (CONT. 1)

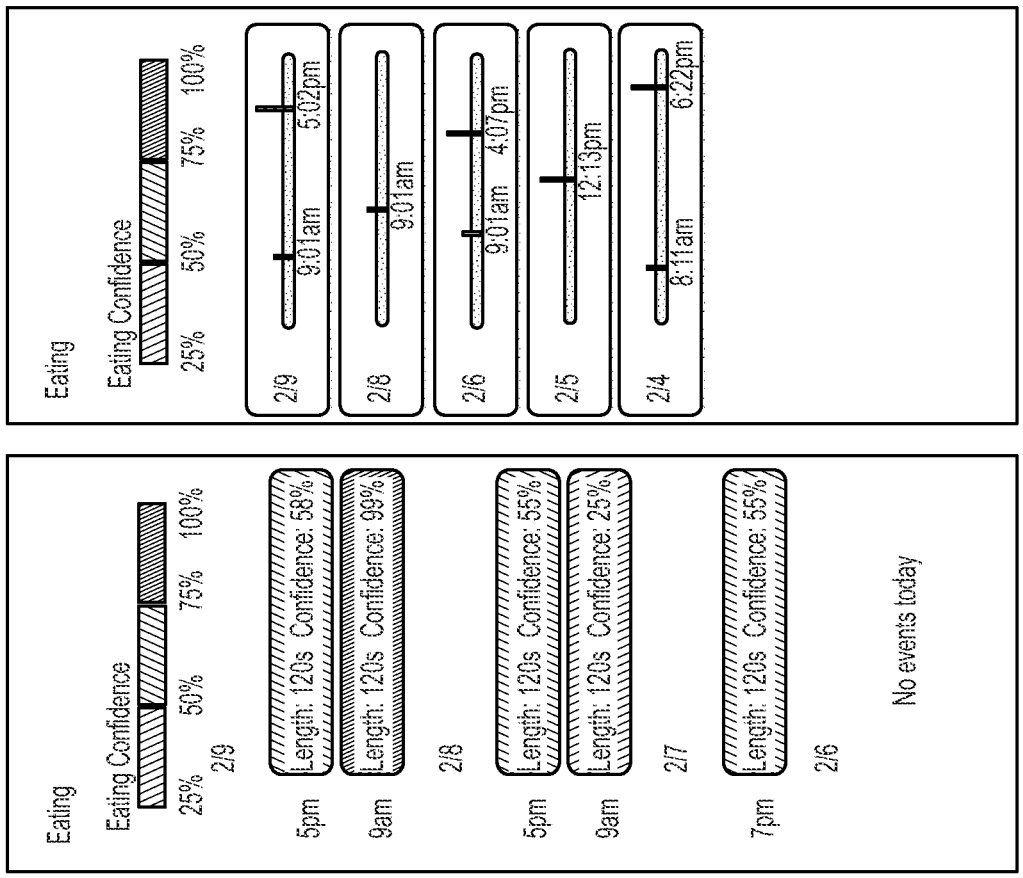
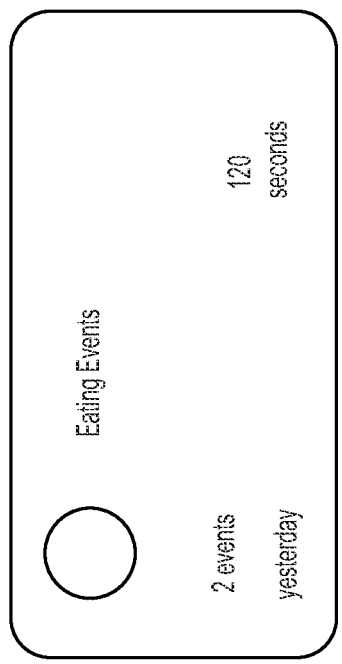
*FIG. 2A*
*FIG. 2B*
*FIG. 2C*

300

```
┌─────────────────────────────────────────────────────────────────────────┐
│ RECEIVING A PLURALITY OF HISTORICAL PET EATING DATA RECORDS FROM A      │
│ DATABASE, EACH RECORD OF THE PLURALITY OF HISTORICAL PET EATING DATA    │
│ RECORDS INCLUDING A HISTORICAL MEAL EVENT VALUE AND A MEAL EVENT DATE   │
│                                  302                                     │
└─────────────────────────────────────────────────────────────────────────┘
                                    ↓
┌─────────────────────────────────────────────────────────────────────────┐
│      DETERMINING A SUBSET OF THE PLURALITY OF HISTORICAL PET EATING     │
│                            DATA RECORDS                                  │
│                                  304                                     │
└─────────────────────────────────────────────────────────────────────────┘
                                    ↓
┌─────────────────────────────────────────────────────────────────────────┐
│ DETERMINING AN EXPECTED DISTRIBUTION BASED ON THE PLURALITY OF HISTORICAL│
│ PET EATING DATA RECORDS, THE EXPECTED DISTRIBUTION INCLUDING A BASELINE, │
│ AN UPPER THRESHOLD, AND A LOWER THRESHOLD, WHEREIN THE UPPER THRESHOLD   │
│         AND THE LOWER THRESHOLD CORRESPOND TO THE BASELINE              │
│                                  306                                     │
└─────────────────────────────────────────────────────────────────────────┘
                                    ↓
┌─────────────────────────────────────────────────────────────────────────┐
│    RECEIVING CURRENT PET DATA FROM A PET SENSOR, THE CURRENT PET DATA   │
│                   INCLUDING A TOTAL MEAL EVENT VALUE                     │
│                                  308                                     │
└─────────────────────────────────────────────────────────────────────────┘
                                    ↓
┌─────────────────────────────────────────────────────────────────────────┐
│   ANALYZING WHETHER THE TOTAL MEAL EVENT VALUE EXCEEDS THE UPPER        │
│                  THRESHOLD OR THE LOWER THRESHOLD                        │
│                                  310                                     │
└─────────────────────────────────────────────────────────────────────────┘
                                    ↓
┌─────────────────────────────────────────────────────────────────────────┐
│    OUTPUTTING A NOTIFICATION INDICATING A RESULT THAT IS RESPONSIVE      │
│                            TO THE ANALYZING                              │
│                                  312                                     │
└─────────────────────────────────────────────────────────────────────────┘
```

```
┌─────────────────────────────────────────────────────────────────────────┐
│ DETERMINING ONE OR MORE HISTORICAL PET EATING DATA RECORDS, OF THE      │
│ PLURALITY OF HISTORICAL PET EATING DATA RECORDS, THAT ARE EACH          │
│ INDICATIVE OF AN OUTLIER                                                │
│ 402                                                                     │
└─────────────────────────────────────────────────────────────────────────┘
                                    │
                                    ▼
┌─────────────────────────────────────────────────────────────────────────┐
│ EXCLUDING THE ONE OR MORE HISTORICAL PET EATING DATA RECORDS THAT ARE   │
│ EACH INDICATIVE OF AN OUTLIER                                           │
│ 404                                                                     │
└─────────────────────────────────────────────────────────────────────────┘
                                    │
                                    ▼
┌─────────────────────────────────────────────────────────────────────────┐
│ DETERMINING ONE OR MORE HISTORICAL PET EATING DATA RECORDS, OF THE      │
│ PLURALITY OF HISTORICAL PET EATING DATA RECORDS, THAT EACH INCLUDE A    │
│ HISTORICAL SENSOR WEARING RATIO LESS THAN A SENSOR WEARING THRESHOLD    │
│ 406                                                                     │
└─────────────────────────────────────────────────────────────────────────┘
                                    │
                                    ▼
┌─────────────────────────────────────────────────────────────────────────┐
│ EXCLUDING THE ONE OR MORE HISTORICAL PET EATING DATA RECORDS THAT EACH  │
│ INCLUDE A HISTORICAL SENSOR WEARING RATIO LESS THAN A SENSOR WEARING    │
│ THRESHOLD                                                               │
│ 408                                                                     │
└─────────────────────────────────────────────────────────────────────────┘
```

```
┌─────────────────────────────────────────────────────────────────────┐
│              DETERMINING WHETHER THE BASELINE IS VALID              │
│   ┌─────────────────────────────────────────────────────────────┐   │
│   │ DETERMINING WHETHER THE SUBSET OF THE PLURALITY OF HISTORICAL PET EATING │   │
│   │    DATA RECORDS COMPRISES A PREDETERMINED NUMBER OF HISTORICAL PET     │   │
│   │    EATING DATA RECORDS THAT ARE EACH ASSOCIATED WITH A HISTORICAL MEAL │   │
│   │              EVENT DATE WITHIN A PREDETERMINED TIME RANGE              │   │
│   │                               504                                      │   │
│   └─────────────────────────────────────────────────────────────┘   │
│   ┌─────────────────────────────────────────────────────────────┐   │
│   │  DETERMINING WHETHER EACH OF THE PREDETERMINED NUMBER OF HISTORICAL   │   │
│   │  PET EATING DATA RECORDS IS FURTHER ASSOCIATED WITH A HISTORICAL SENSOR│   │
│   │   WEARING RATIO MEETING OR EXCEEDING A BASELINE SENSOR WEARING        │   │
│   │                              THRESHOLD                                │   │
│   │                                506                                    │   │
│   └─────────────────────────────────────────────────────────────┘   │
│                                 502                                 │
└─────────────────────────────────────────────────────────────────────┘
                                   │
                                   ▼
┌─────────────────────────────────────────────────────────────────────┐
│ IN RESPONSE TO DETERMINING THAT THE BASELINE IS VALID, DISPLAYING THE BASELINE │
│                         VIA A USER INTERFACE                        │
│                                 508                                 │
└─────────────────────────────────────────────────────────────────────┘
```

*FIG. 5*

SYSTEMS AND METHODS FOR DETECTING EATING PATTERNS OF A PET

CROSS-REFERENCE TO RELATED APPLICATION(S)

This patent application claims the benefit of priority to U.S. Provisional Application No. 63/286,721, filed Dec. 7, 2021, which is incorporated herein by reference in its entirety.

TECHNICAL FIELD

Various embodiments of this disclosure relate generally to detecting eating patterns of a pet. In some embodiments, the disclosure relates to systems and methods for using historical pet eating data to determine changes in pet eating behavior.

BACKGROUND

A pet's appetite and corresponding eating habits are important indicators of how the pet is feeling. For example, a pet spending more or less time than average eating may indicate a health issue, such as a tooth problem. Eating detection and analysis can be an incredibly useful tool for catching potential pet issues before such issues become large problems.

Conventional methods may include relying on the pet parent to track and record when a pet eats a meal. However, pet parents do not always see everything that a pet does or does not eat and subtle eating trends can be hard to catch. For example, conventional methods may fail to include the possibility that the pet is stealing food from other pet sources, or that the pet's food is being stolen by other pets. Furthermore, conventional techniques may also fail to take unexpected eating events, such as eating events that take place when the pet parent is away, into account during the eating detection process.

Additionally, conventional methods may not dynamically adapt to individual pet's eating behavior. However, eating detection is not a one-size-fits-all method. For example, pet breeds, as well as individual pets, have different eating styles. Smaller pet breeds tend to nibble food throughout the day, instead of eating 2-3 large meals, which may make eating detection even more challenging.

This disclosure is directed to addressing above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, methods and systems are disclosed for using historical pet eating data to determine changes in pet eating behavior.

In one aspect, an exemplary embodiment of a method for using historical pet eating data to determine changes in pet eating behavior includes receiving, by one or more processors, a plurality of historical pet eating data records from a database, each record of the plurality of historical pet eating data records including a historical meal event value and a meal event date. The method may further include determining, by the one or more processors, a subset of the plurality of historical pet eating data records. The method may further include determining, by the one or more processors, an expected distribution based on the subset of the plurality of historical pet eating data records, the expected distribution including a baseline, an upper threshold, and a lower threshold, wherein the upper threshold and the lower threshold correspond to the baseline. The method may further include receiving, by the one or more processors, current pet data from a pet sensor, the current pet data including a total meal event value. The method may further include analyzing, by the one or more processors, whether the total meal event value exceeds the upper threshold or the lower threshold, and outputting, by the one or more processors, a notification indicating a result that is responsive to the analyzing.

In a further aspect, an exemplary embodiment of a computer system for using historical companion pet eating data to determine changes in companion pet eating behavior is disclosed, the computer system comprising at least one memory storing instructions, and at least one processor configured to execute the instructions to perform operations. The operations may include receiving a plurality of historical pet eating data records from a database, where each record of the plurality of historical pet eating data records including a historical meal event value and a meal event date. The operations may further include determining a subset of the plurality of historical pet eating data records. The operations may further include determining an expected distribution based on the subset of the plurality of historical pet eating data records, the expected distribution including a baseline, an upper threshold, and a lower threshold, wherein the upper threshold and the lower threshold correspond to the baseline. The operations may further include receiving current pet data from a pet sensor, the current pet data including a total meal event value, analyzing whether the total meal event value exceeds the upper threshold or the lower threshold, and outputting a notification indicating a result that is responsive to the analyzing.

In a further aspect, a non-transitory computer-readable medium containing instructions that, when executed by a processor, cause the processor to perform operations for using historical companion pet eating data to determine changes in companion pet eating behavior is disclosed. The operations may include receiving a plurality of historical pet eating data records from a database, where each record of the plurality of historical pet eating data records including a historical meal event value and a meal event date. The operations may further include determining a subset of the plurality of historical pet eating data records. The operations may further include determining an expected distribution based on the subset of the plurality of historical pet eating data records, the expected distribution including a baseline, an upper threshold, and a lower threshold, wherein the upper threshold and the lower threshold correspond to the baseline. The operations may further include receiving current pet data from a pet sensor, the current pet data including a total meal event value, analyzing whether the total meal event value exceeds the upper threshold or the lower threshold, and outputting a notification indicating a result that is responsive to the analyzing.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 2A-2C describe exemplary environments of a platform for analyzing and displaying a pet's eating data, according to one or more embodiments FIG. 3 depicts a flowchart of an exemplary method for using historical pet eating data to determine changes in pet eating behavior, according to one or more embodiments.

FIG. 4 depicts a flowchart further illustrating an exemplary method for determining a subset of a plurality of historical pet eating data records to determine an expected distribution, according to one or more embodiments.

FIG. 5 depicts a flowchart further illustrating an exemplary method for determining whether a baseline of an expected distribution is valid, according to one or more embodiments.

DETAILED DESCRIPTION OF EMBODIMENTS

According to certain aspects of the disclosure, methods and systems are disclosed for detecting and analyzing eating patterns of a pet. Conventional techniques may not be suitable because conventional techniques may rely on the pet parent to track and record the pet's eat events. Additionally, conventional techniques may not dynamically adapt to the pet's individual eating habits. Accordingly, improvements in technology relating to detecting and analyzing eating patterns of a pet are needed.

A pet's eating time is very important. For example, if a pet is spending more or less time than average eating, a pet parent may want to check for a potential health issue. Longer eating times could indicate that the pet is eating more carefully or not feeling as hungry. Potential health issues corresponding to a change in eating may include dental issues, gastrointestinal issues, or pickiness of the pet. Simple changes, such as changing a food bowl, a food type, and/or the food shape may also impact a pet's eating habits.

A need exists for eating detection techniques that detect a pet's eating events, as well as analyze the eating events to determine eating event patterns. The eating detection techniques disclosed herein may objectively show pet parents if a pet's eating behavior is changing. Such changes in a pet's eating behavior may be indicative of potential health issues and/or may indicate that a pet should be fed more or less food. Additionally, the pet parent may also be able to share the pet's eating event information with the pet's veterinarian to help provide context regarding what is happening in the day to day life of the pet.

As will be discussed in more detail below, in various embodiments, systems and methods are described for using historical pet eating data to determine changes in pet eating behavior. By collecting and analyzing historical pet eating data, the systems and methods may be able to calculate an expected distribution for future pet eating events, where the expected distribution may include a baseline, an upper threshold, and a lower threshold. The systems and methods may then receive current pet eating data and compare such pet eating data to the expected distribution. The systems and methods may then output a notification indicating a result of the comparison to notify the pet parent of any changes in the pet's eating data.

Exemplary Wellness Data Platform

FIGS. 1A-J describe exemplary environments of a platform for analyzing and displaying a pet's wellness data, according to one or more embodiments.

Figure 1A:
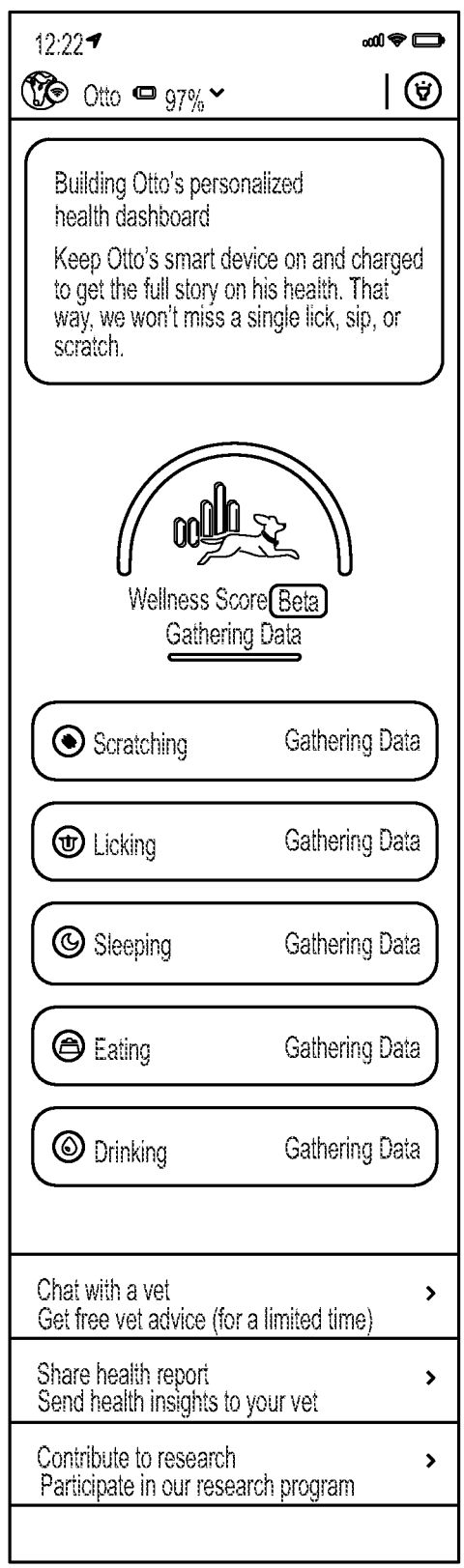
FIGS. 1A-1J describe exemplary environments of a platform for analyzing and displaying a pet's wellness data, according to one or more embodiments.

FIG. 1A illustrates a "Dashboard" page of an exemplary environment of a platform for gathering, analyzing, and displaying a pet's data, according to one or more embodiments. The platform may display a pet's overall Wellness Score, as well as one or more of the following behavior sections: "Scratching," "Licking," "Sleeping," "Eating," and/or "Drinking." The platform may also display an option to communicate with a vet (e.g., "Chat with a vet"), send the summary data to a recipient (e.g., "Share health report"), and/or participate in a research program (e.g., "Contribute to research").

Additionally, the platform may display the "Dashboard" page during initial stages of when the data is still being gathered from a pet. For example, if data is still being collected from the pet, there may not be enough data to analyze and display. As a result, the platform may display a "Gathering Data" value for one or all of the displayed Wellness Score, scratching data, licking data, sleeping data, eating data, and/or drinking data.

Figure 1B:
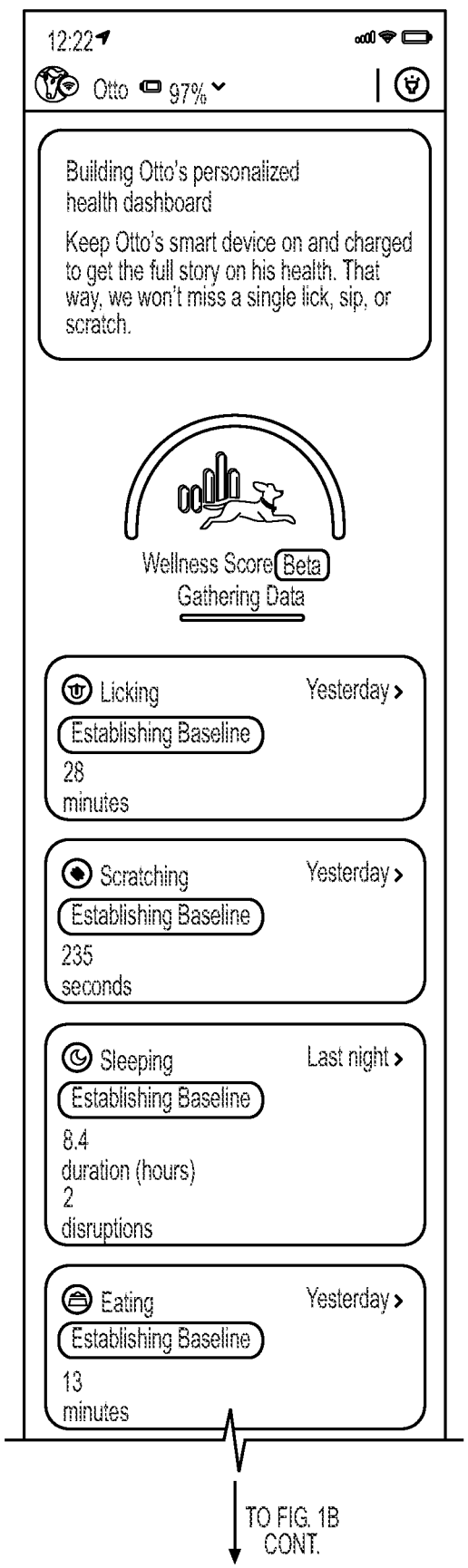

FIG. 1B further illustrates a "Dashboard" page of an exemplary environment of a platform for gathering, analyzing, and displaying a pet's wellness data, according to one or more embodiments.

The platform may display a pet's overall Wellness Score, as well as one or more of the following behavior sections: "Scratching," "Licking," "Sleeping," "Eating," and/or "Drinking." If the platform is still gathering data to establish a baseline, the platform may display an "Establishing Baseline" for any of the displayed behavior sections. In some embodiments, while the platform is in the process of establishing a baseline, the platform may display a value for the duration of the behavior in the corresponding behavior's section (e.g., "28 minutes" in the "Licking" section, "235 seconds" in the "Scratching" section, "8.4 duration (hours)" with "2 disruptions" in the "Sleeping" section, "13 minutes" in the "Eating" section, and/or "2 minutes" in the "Drinking" section). For example, the duration may be expressed in seconds, minutes, and/or hours. The platform may also display an option to communicate with a vet (e.g., "Chat with a vet"), send the summary data to a recipient (e.g., "Share health report"), and/or participate in a research program (e.g., "Contribute to research").

Figure 1C:
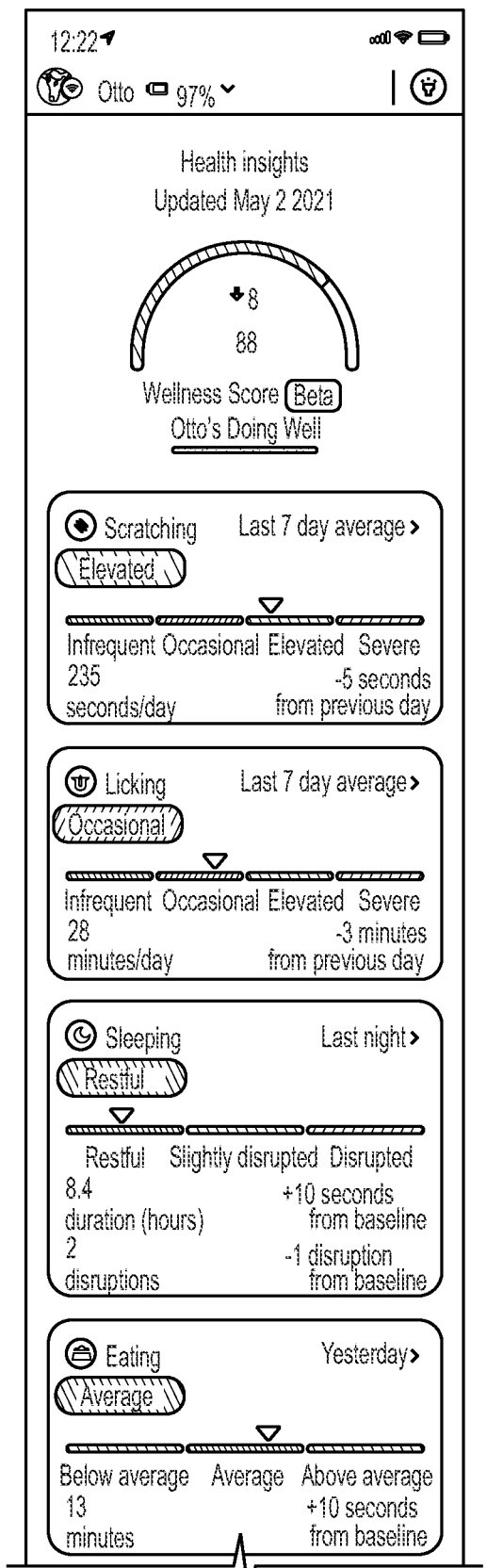

FIG. 1C further illustrates a "Health Insights" page of an exemplary environment of a platform for gathering, analyzing, and displaying a pet's wellness data, according to one or more embodiments.

Figure 1D:
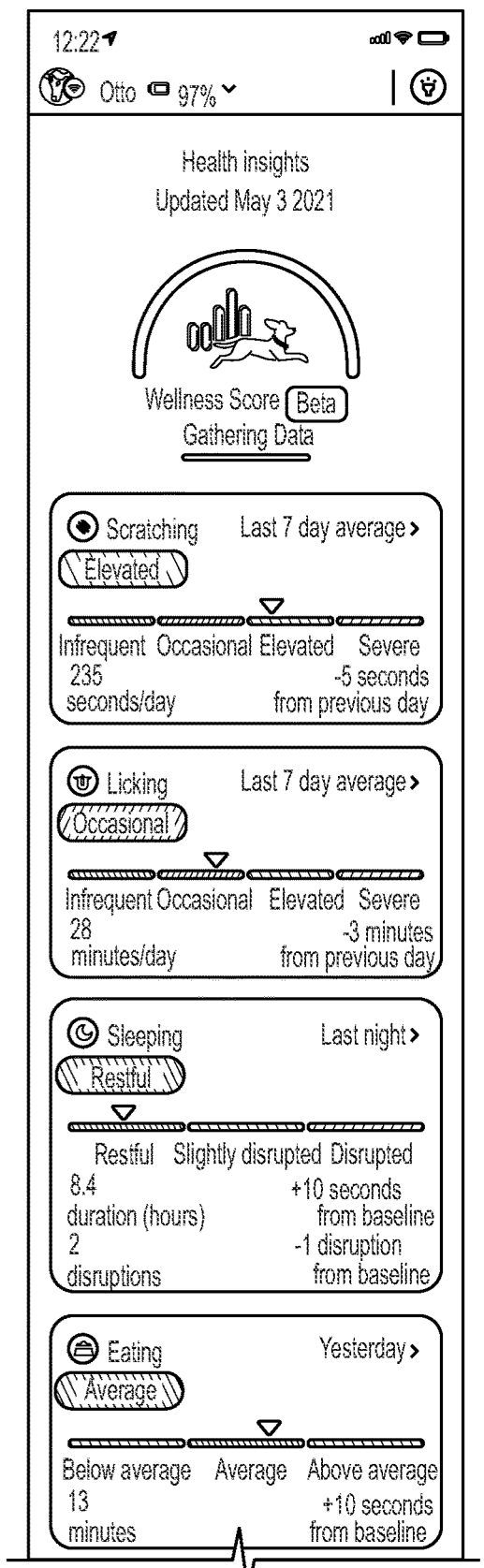

The platform may display a pet's overall Wellness Score, as well as one or more of the following behavior sections: "Scratching," "Licking," "Sleeping," "Eating," and/or "Drinking." The pet's overall Wellness Score may be based on an overall analysis of all (or some) of the behaviors (e.g., "88"). The platform may also display an image indicating where the Wellness Score fits on a scale, as well as a comparison of how the Wellness Score compares to previous Wellness Scores (e.g. a decrease of "8" from a previous score, indicated by the value "8" and the downward arrow in FIG. 1C). The platform may further display a written description of the pet's current health condition based on the Wellness Score (e.g., "Otto's Doing Well"). In some embodiments, as illustrated in FIG. 1D, if the platform does not have enough data to display an overall Wellness Score, the platform may display an indicator stating that the platform is "Gathering Data."

Once the platform has established a baseline for a particular behavior section, the platform may display an image that indicates how the pet's current behavior compares to the behavior baseline. For example, in the "Scratching" section, the pet's current behavior may be "Infrequent," "Occasional," "Elevated," and/or "Severe" when compared to the pet's scratching baseline. Additionally, in the "Licking" section, the pet's current behavior may be "Infrequent," "Occasional," "Elevated," and/or "Severe" when compared to the pet's licking baseline. In the "Sleeping" section, the pet's current behavior may be "Restful," "Slightly disrupted," and/or "Disrupted" when compared to the pet's sleeping baseline. In the "Eating" section, the pet's current eating behavior may be "Below average," "Average," and/or "Above average" when compared to the eating baseline. In the "Drinking" section, the pet's current drinking behavior may be "Below average," "Average," and/or "Above average" when compared to the drinking baseline.

The platform may also display a duration of a behavior, an average duration of the behavior, a previous duration of the behavior, and/or how the behavior compares to a previous time period, such as a previous day. For example, in the "Scratching" section, the platform may display an average duration of "235 seconds/day" with a behavior comparison of "−5 seconds from previous day." In the "Licking" section, the platform may display an average duration of "28 minutes/day" with a behavior comparison of "−3 minutes from previous day." In the "Sleeping" section, the platform may display "8.4 duration (hours)" with a behavior comparison of "+10 seconds from baseline." A number of disruptions may also be displayed (e.g., "2 disruptions") and/or how the disruptions compare to a disruption baseline (e.g., "−1 disruption from baseline"). In the "Eating" section, the platform may display a previous duration of the behavior of "13 minutes" with a behavior comparison of "+10 seconds from baseline." In the "Drinking" section, the platform may display a previous duration of the behavior of "2 minutes" with a behavior comparison of "+10 seconds from baseline."

The platform may also display an option for viewing the previous and/or current data. If a user selects the option, the platform may display more details of the previously collected data. For example, in the "Scratching" section, the platform may display an option to view the "Last 7 day average." In the "Licking" section, the platform may display an option to view the "Last 7 day average." In the "Sleeping" section, the platform may display an option to view the details of "Last night." In the "Eating" section, the platform may display an option to view the details of "Yesterday." In the "Drinking" section, the platform may display an option to view the details of "Yesterday." The platform may also display an option to communicate with a vet (e.g., "Chat with a vet"), send the summary data to a recipient (e.g., "Share health report"), and/or participate in a research program (e.g., "Contribute to research").

Figure 1E:
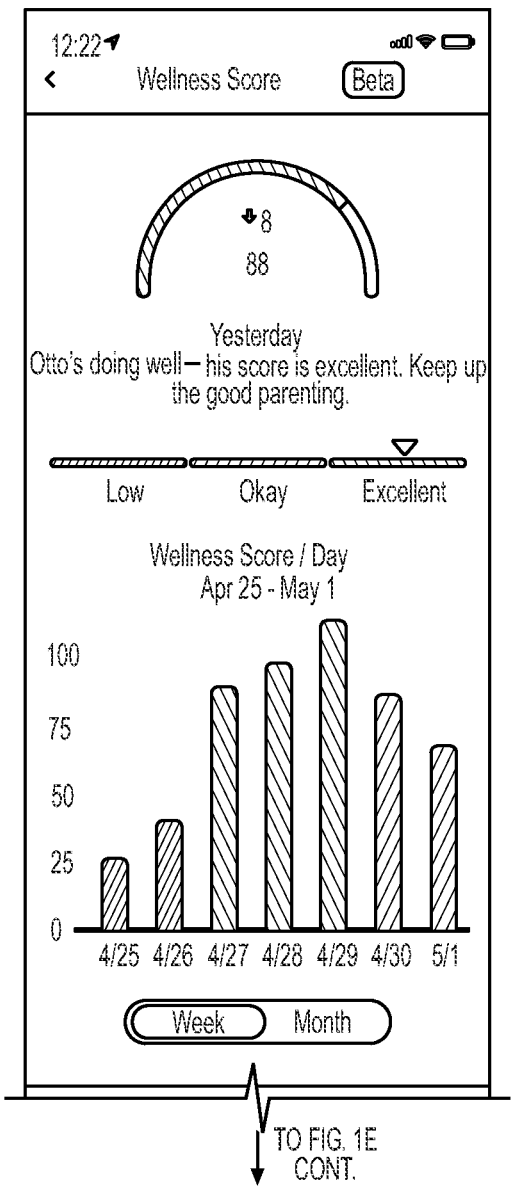

FIG. 1E further illustrates a "Wellness Score" page of an exemplary environment of a platform for gathering, analyzing, and displaying a pet's wellness data, according to one or more embodiments.

The platform may display a Wellness Score (e.g., "88") and/or a half ring or an arc indicating where the Wellness Score falls on a spectrum. The Wellness Score may correspond to the health of the pet. For example, the Wellness Score may be based on an analysis of one or all of the pet behaviors. The platform may also display an indicator corresponding to a label of the Wellness Score (e.g., "Low," "Okay," and/or "Excellent"). The "Low" label may correspond to a score of 0-59, an "Okay" label may correspond to a score of 60-79, and an "Excellent" label may correspond to a score of 80-100. In some embodiments, the labels may have corresponding colors. For example, the color red may correspond to a "Low" label, the color yellow may correspond to the "Okay" label, and the color green may correspond to an "Excellent" label. In some embodiments, the platform may display a bar graph that indicates the Wellness Score for one or more previous days and/or one or more previous months. The graph may also be color coded, where the color for a particular day corresponds to a color of a label of the Wellness Score.

Figure 1F:
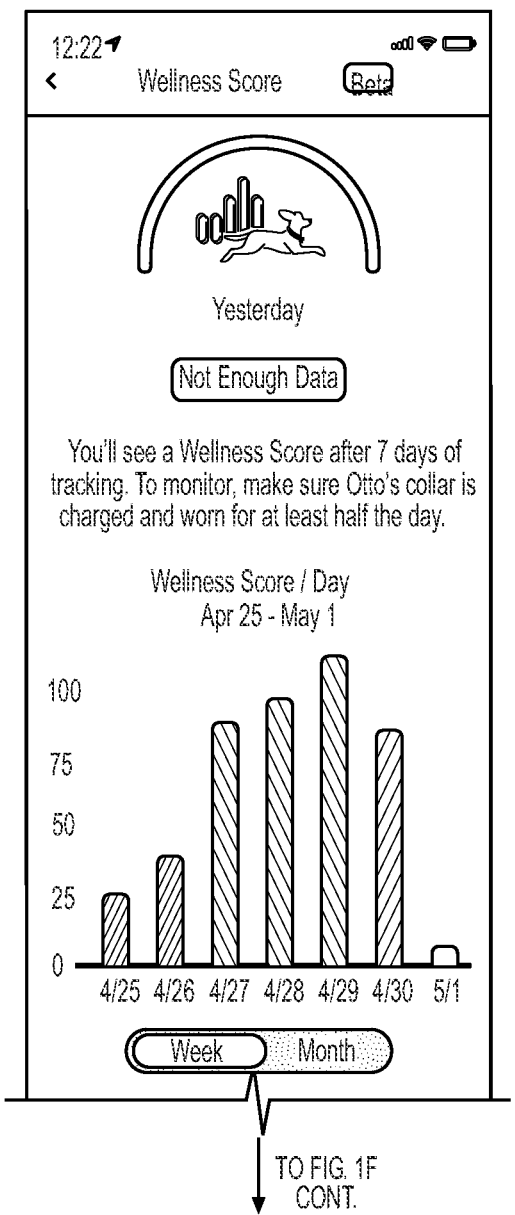

In some embodiments, as shown in FIG. 1F, if there is not enough data to produce a Wellness Score, the platform may display a "Not Enough Data" label. Additionally, the "Not Enough Data" label may have a corresponding color, such as gray. For example, if one or more days in the displayed graph have a "Not Enough Data" label, the graph may display the color gray for the one or more days that have a "Not Enough Data" label.

The platform may also display an option to learn more about the eating metrics (e.g., "Learn about eating levels") and/or get vet advice (e.g., "Chat with a vet").

Figure 1G:
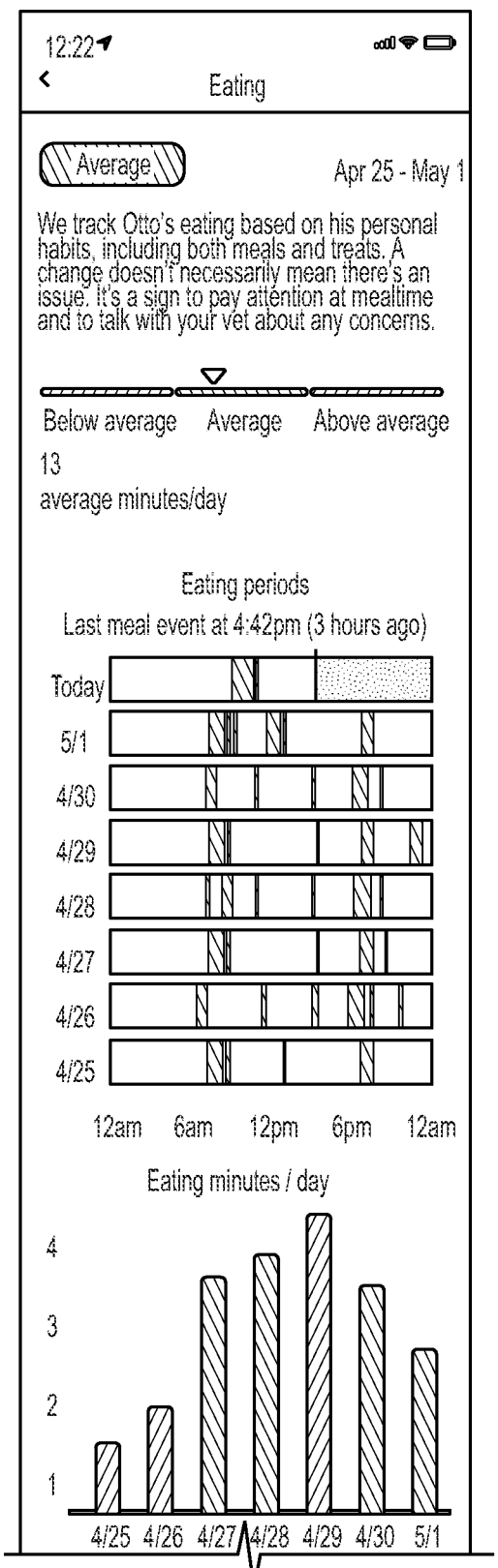

FIG. 1G further illustrates an "Eating" page of an exemplary environment of a platform for gathering, analyzing, and displaying a pet's wellness data, according to one or more embodiments.

The platform may display if the pet's current eating behavior is "below average," "average," and/or "above average" when compared to the pet's eating baseline. The platform may further display an average amount of time that the pet spends eating (e.g., "13 average minutes/day").

The platform may also display a graph of the eating periods of the pet, which may track all of the meal events of the pet. In some embodiments, the eating period data may have been captured by a sensor and/or an electronic device worn by the pet. The eating periods may be displayed in the form of a graph, where the graph may include a date on the y-axis and time periods on the x-axis. The graph may include blocks that indicate the beginning of a time period where the pet begins eating, as well as an end of a time period that the pet stops eating. The platform may also display when the most recent meal event took place (e.g., "Last meal event at 4:42 pm (3 hours ago)").

Figure 1H:
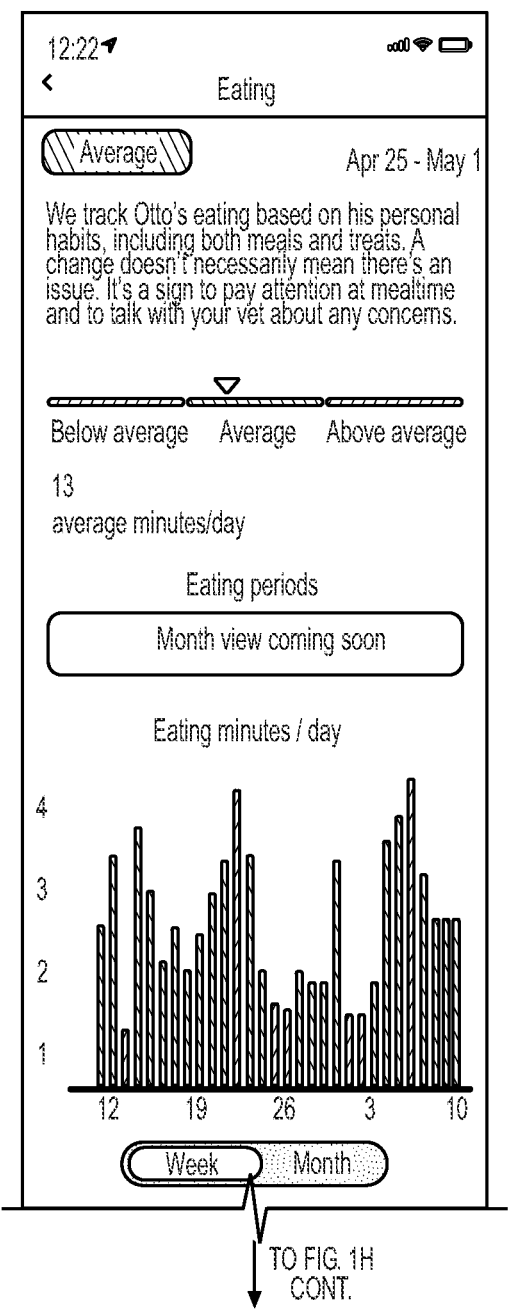
Figure 1I:
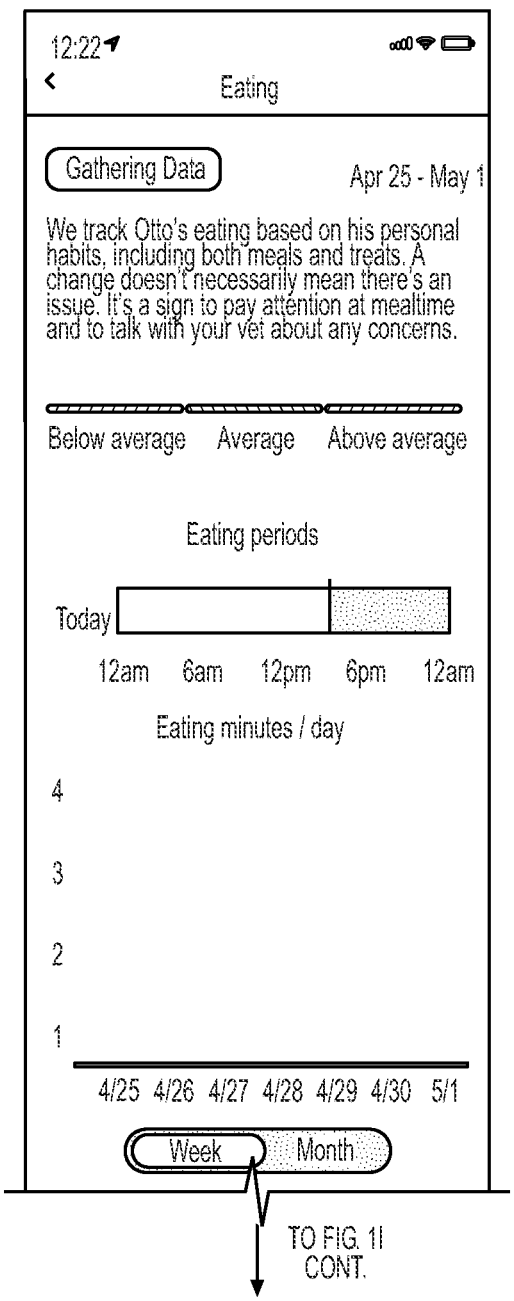

The platform may also display a bar graph that provides a visual representation of the number of minutes a pet eats per day on a weekly basis (as shown in FIG. 1G) or a monthly basis (as shown in FIG. 1H). The platform may display the bars in a color corresponding to whether the pet's eating for the particular day was "below average," "average," and/or "above average" when compared to the pet's eating baseline. In some embodiments, if the platform is in the process of collecting eating data of the pet, the graphs may not display any data (as shown in FIG. 1I).

The platform may also display an option to learn more about the eating metrics (e.g., "Learn about eating levels") and/or talk to a vet (e.g., "Chat with a vet").

Figure 1J:
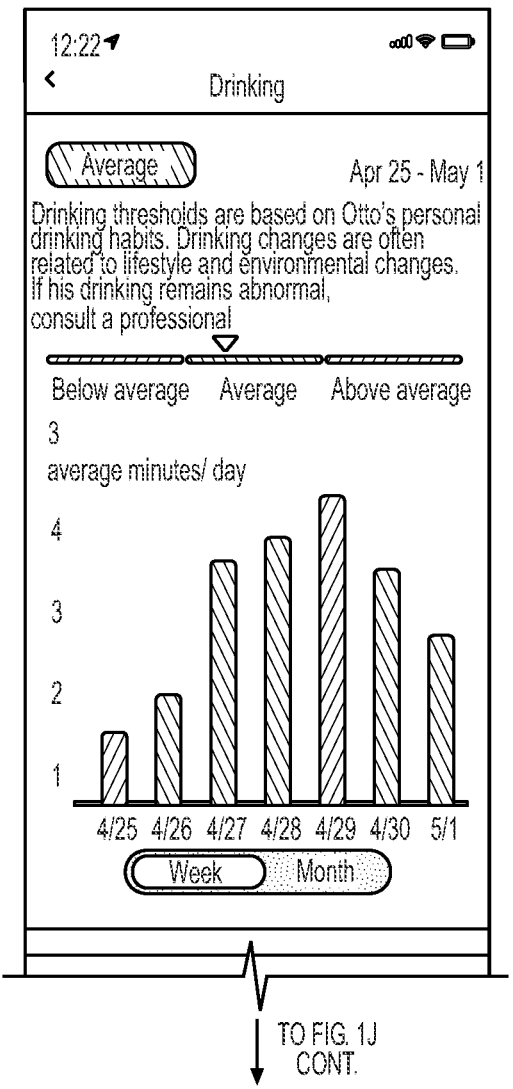

FIG. 1J further illustrates a "Drinking" page of an exemplary environment of a platform for gathering, analyzing, and displaying a pet's wellness data, according to one or more embodiments.

The platform may display whether the pet's current drinking behavior is "below average," "average," and/or "above average" when compared to the pet's drinking baseline. The platform may further display an average amount of time that the pet spends drinking (e.g., "3 average minutes/day").

The platform may also display a bar graph that provides a visual representation of the number of minutes a pet spends drinking per day on a weekly basis or a monthly basis. The platform may also display the bars in a color corresponding to whether the pet's drinking on a particular day was "below average," "average," and/or "above average" when compared to the pet's drinking baseline. In some embodiments, if the platform is in the process of collecting drinking data of the pet, the graph may not display any data.

Exemplary Eating Data Platform

FIGS. 2A-C describe exemplary environments of a platform for analyzing and displaying a pet's eating data, according to one or more embodiments.

FIG. 2A illustrates an "Eating Events" interface of an exemplary environment of a platform for displaying a pet's eating data, according to one or more embodiments. The platform may display the number of eating events that occur over a particular time period (e.g., "2 events yesterday"). The eating events may correspond to the number of times that the pet eats food, treats, etc. In some embodiments, a sensor and/or an electronic device worn by the pet may capture the eating events. The platform may also display the amount of time that the pet spends eating (e.g., "120 seconds"). The amount of time that the pet spends eating may correspond to the sum of the length of the eating events. Additionally, for example, the amount of time that the pet spends eating may be described as seconds, minutes, and/or hours.

FIG. 2B illustrates an "Eating" interface of an exemplary environment of a platform for displaying a pet's eating data, according to one or more embodiments. The platform may display each eating event that occurred during a particular time period, such as a day, a month, or a year. The platform may provide a list of the eating events that occurred during the particular time period (e.g., "⅖"). In some embodiments, each displayed eating event may include a length (e.g., "Length: 120 s") and/or a confidence level (e.g., "Confidence: 58%"). The length may correspond to the duration of the particular eating event. The confidence level may correspond to how confident the platform is regarding the eating event determination. Additionally, in some embodiments, each of the eating events may be a particular color shade, where the color shade corresponds to the confidence level. For example, the color shade of the eating event may be darker when the confidence level is higher (e.g., a dark green when the confidence level is 99%) and lighter when the confidence level is lower (e.g., a light green when the confidence level is 25%).

FIG. 2C illustrates an "Eating" interface of an exemplary environment of a platform for displaying a pet's eating data, according to one or more embodiments. The platform may display, for a particular time period, such as a day, month, and/or year, a timeline corresponding to the particular period of time. In some embodiments, the platform may indicate a line that is placed at the time of the occurrence of the eating event. Additionally, for example, the line may have a particular color shade that corresponds to a confidence level of the eating event, where the confidence level may correspond to the platform's confidence in determining the eating event.

Exemplary Method for Determining Changes in Pet Eating Behavior

FIG. 3 illustrates an exemplary process 300 for using historical pet eating data to determine changes in pet eating behavior, according to one or more embodiments.

The method may include receiving, by one or more processors, a plurality of historical pet eating data records from a database, each record of the plurality of historical pet eating data records includes a historical meal event value and a meal event date (Step 302). The database may store each of the historical pet eating data records in real-time. Alternatively, the database may store each of the historical pet eating data records after a predetermined time, such as at the end of a day. The database may receive the historical pet eating data from a pet sensor and/or an electronic device worn by the pet, where the pet sensor and/or electronic device captures the eating events in real-time. The pet sensor and/or electronic device may continuously communicate the historical pet eating data to the database in real-time or after a predetermined period of time. For example, the pet sensor and/or the electronic device may send the most current historical pet eating data to the database every minute, every hour, every day, every week, etc. Upon receiving the historical pet eating data, the database may store such historical pet eating data in a historical pet eating data record. Additionally, if the database has already received and stored historical pet eating data in a historical pet eating data record for a particular meal event date, the database may override/update such stored historical pet eating data record with the most recent received historical pet eating data for the meal event date.

Each record of the plurality of historical pet eating data records may include a historical meal event value and a meal event date. The historical meal event value may include a sum total of the duration of all eating events that occur on the meal event date. For example, the historical meal event value may be "120 seconds," which may be the total length of time that the pet spent eating, and the meal event date may be "Feb. 1, 2021." The historical meal event value may be expressed in seconds, minutes, and/or hours.

Additionally, each of the historical pet eating data records may also include a historical pet identifier and/or a historical sensor wearing ratio. The historical pet identifier may include a unique identifier corresponding to the sensor and/or electronic device worn by the pet. The historical sensor wearing ratio may correspond to a time ratio that the pet wore the pet sensor on the meal event date. For example, the historical sensor wearing ratio may be 0.5, which may mean that the pet wore the sensor 50% of the time on the meal event date.

The method may further include determining, by the one or more processors, a subset of the plurality of historical pet eating data records (Step 304). The subset of the plurality of historical pet eating data records may include at least one pet eating data record. In some embodiments, the subset of the plurality of historical pet eating data records may include all of the plurality of historical pet eating data records. In some embodiments, the subset may be stored in a database. The process of determining a subset of the plurality of historical pet eating data records may be further discussed in Steps 402-408 in FIG. 4.

The method may further include determining, by the one or more processors, an expected distribution based on the subset of the plurality of historical pet eating data records, the expected distribution including a baseline, an upper threshold, and a lower threshold, wherein the upper threshold and the lower threshold correspond to the baseline (Step 306). The baseline may be an expected total meal event length, which may be based on an average of the historical meal event values corresponding to the subset of the plurality of historical pet eating data records. The baseline may be updated each time period (e.g., each day) based on the most current average of historical meal event values. In some embodiments, the baseline may be an average of the subset of the plurality of historical pet eating data records that do not include one or more existing outliers (further described in Steps 402-408). Steps 502-508 in FIG. 5 further describe determining the validity of the baseline.

The upper threshold and the lower threshold may correspond to the baseline, where the upper threshold and/or the lower threshold may provide a range for the total meal event length. For example, the upper threshold and the lower threshold may be set at +/−0.84 standard deviations from the baseline. This would result in about 40% of a pet's day being considered either above or below average (20% for the upper threshold and 20% for the lower threshold), with 60% of the pet's day being considered average. The upper threshold and/or the lower threshold may provide flexibility. For example, if the pet eats an additional meal, such behavior may be considered in the upper threshold ("above average"). Additionally, for example, if a pet misses a meal, such behavior may be considered in the lower threshold ("below average").

The method may further include receiving, by the one or more processors, current pet data from a pet sensor, the current pet data including a total meal event value (Step 308). The pet sensor may be a pet sensor and/or an electronic device worn by the pet. The current pet data may also include a pet identifier, a corresponding date, and/or a sensor wearing ratio. The pet identifier may include a unique identifier corresponding to the pet sensor. The corresponding date may include a date that corresponds to when the total meal event value took place. The pet sensor wearing ratio may correspond to a time ratio that the pet wore the pet sensor on the corresponding date. The total meal event value may include a sum of a duration of all meal events that occurred on the corresponding date. For example, the total meal event value may be "50 seconds," which may be the total length of time that the pet spent eating, and the corresponding date may be "Dec. 21, 2021." Additionally, for example, the total meal event value may be measured in seconds, minutes, and/or hours.

The method may also include analyzing, by the one or more processors, whether the total meal event value exceeds the upper threshold or the lower threshold (Step 310). The total meal event value may be compared against the upper threshold and the lower threshold. For the purposes of the current disclosure, the total meal event value may exceed the upper threshold if the total meal event value is greater than the upper threshold, and the total meal event value may exceed the lower threshold if the total meal event value is less than the lower threshold.

The method may also include outputting, by the one or more processors, a notification indicating a result that is responsive to the analyzing (Step 312). The outputting may result in displaying the notification on a user interface of an electronic device, such as a mobile phone. The notification may also be in the form of an alert and/or a graphical image, such as a graph. FIGS. 1F-H may be exemplary user interfaces.

The notification may include at least one of: an eating above average notification, an eating average notification, or an eating below average notification. The eating above average notification may indicate that the pet is eating more than usual. For example, the eating above average notification may correspond to the total meal event value meeting or exceeding the upper threshold. The eating above average notification may be related to the pet eating extra treats, a larger helping at meal time, or a longer meal event than normal. The eating average notification may indicate that the pet is eating normally. For example, the eating average notification may correspond to the total meal event value being equal to or below the upper threshold and equal to or above the lower threshold. The eating below average notification may indicate that the pet is eating less than usual. For example, the eating below average notification may correspond to the total meal event value meeting or exceeding the lower threshold. The eating below average notification may be related to the pet missing a treat (or two), a smaller helping at meal time, or a faster meal event than normal.

Although FIG. 3 shows example blocks of exemplary method 300, in some implementations, the exemplary method 300 may include additional blocks, fewer blocks, different blocks, or differently arranged blocks than those depicted in FIG. 3. Additionally, or alternatively, two or more of the blocks of the exemplary method 300 may be performed in parallel.

FIG. 4 illustrates an exemplary method 400 for determining a subset of the plurality of historical pet eating data records, according to one or more embodiments. Notably, method 400 of FIG. 4 corresponds to Step 304 of FIG. 3.

The method may include determining one or more historical pet eating data records, of the plurality of historical eating data records, that are each indicative of an outlier (Step 402). For example, determining whether a historical pet eating data record is indicative of an outlier may include determining whether the historical pet eating data record meets or exceeds an outlier threshold value. Such a determination may include subtracting the baseline value of the historical pet eating data record from the total meal event value, and then dividing the result by the square root of the variance for the expected distribution. For example, if the result meets or exceeds a predetermined outlier threshold value, the method may skip/exclude the historical pet eating data record (Step 404) and proceed to analyzing the next historical pet eating data record in the plurality of historical pet eating data records.

The method may further include excluding the one or more historical pet eating data records that are each indicative of an outlier (Step 404). As described in Step 402, if the analysis of the historical pet eating data record meets or exceeds an outlier threshold value, the method may further include excluding the historical pet eating data record. In some embodiments, excluding the one or more historical pet eating data records may include skipping the one or more historical pet eating data records and not including such records in the subset of the plurality of historical pet eating data records. Additionally, in some embodiments, excluding the one or more historical pet eating data records may include removing the one or more historical pet eating data records from the database.

The method may further include determining one or more historical pet eating data records, of the plurality of historical eating data records, that each include a historical sensor wearing ratio less than a sensor wearing threshold (Step 406). In some embodiments, a sensor wearing threshold may exist to ensure that the pet has worn a pet sensor for a minimum amount of time, where the pet sensor wearing threshold may correspond to a ratio of time that the pet has worn the pet sensor. For example, the historical sensor wearing ratio may have a value of 0.5, which may mean that the sensor has been worn for at least 50% of each day of the consecutive days.

In some embodiments, the historical sensor wearing ratio of the one or more historical pet eating data records, which have not been excluded in Step 404, may be compared to the sensor wearing threshold. The one or more historical pet eating data records that have a historical sensor wearing ratio that meets or exceeds the sensor wearing threshold may be added to the subset of the plurality of historical pet eating data records. Additionally, one or more historical pet eating data records that have a historical sensor wearing ratio less than the sensor wearing threshold may be excluded from the subset of the plurality of historical pet eating data records (described further in Step 408).

The method may further include excluding the one or more historical pet eating data records that each include a historical sensor wearing ratio less than a sensor wearing threshold (Step 408). As previously described in Step 406, one or more historical pet eating data records may be excluded if the one or more historical pet eating data records each have a historical sensor wearing ratio less than the sensor wearing threshold. In some embodiments, excluding the one or more historical pet eating data records may include skipping the one or more historical pet eating data records and not including such records in the subset of the plurality of historical pet eating data records. Additionally, in some embodiments, excluding the one or more historical pet eating data records may include removing the one or more historical pet eating data records from the database.

Although FIG. 4 shows example blocks of exemplary method 400, in some implementations, the exemplary method 400 may include additional blocks, fewer blocks, different blocks, or differently arranged blocks than those depicted in FIG. 4. Additionally, or alternatively, two or more of the blocks of the exemplary method 400 may be performed in parallel.

FIG. 5 illustrates an exemplary method 500 for determining whether a baseline is valid, according to one or more embodiments. Notably, method 500 of FIG. 5 may correspond or be relevant to Step 306 of FIG. 3 in one or more aspects.

The method may include determining whether the baseline is valid (Step 502), which may be described in further detail below in Step 504 and Step 506. The baseline may be determined based on the subset of the plurality of historical pet eating data records that do not include one or more outliers, as discussed in Steps 402-408.

The method may include determining whether the subset of the plurality of historical pet eating data records comprises a predetermined number of historical pet eating data records that are each associated with a meal event date within a predetermined time range (Step 504). In some embodiments, in order to establish the baseline, the subset may need to include a predetermined number of historical pet eating data records that are each associated with a meal event date within a predetermined time range, in order to make sure enough data has been acquired to establish the baseline. The predetermined time range may be days, weeks, months, and/or years. For example, the predetermined number of historical pet eating data records may have a value of seven, where the predetermined time range may be 30 days. Such an example would result in determining whether the subset comprises at least seven historical pet eating data records that have meal event dates within the past 30 days.

The method may include determining whether each of the predetermined number of historical pet eating data records is further associated with a historical sensor wearing ratio meeting or exceeding a baseline sensor wearing threshold (Step 506). In some embodiments, the historical sensor wearing ratio of the one or more historical pet eating data records may be compared to a baseline sensor wearing threshold. If each of the one or more historical pet eating data records has a historical sensor wearing ratio that meets or exceeds the baseline sensor wearing threshold, the baseline may be determined to be valid.

The method may further include, in response to determining that the baseline is valid, displaying the baseline via a user interface (Step 508). For example, the baseline may be displayed on a user interface of a mobile device. The baseline may be displayed as a chart, a graph, etc. Additionally, the baseline may be displayed according to exemplary environments shown in FIGS. 1A-1J.

Although FIG. 5 shows example blocks of exemplary method 500, in some implementations, the exemplary method 500 may include additional blocks, fewer blocks, different blocks, or differently arranged blocks than those depicted in FIG. 5. Additionally, or alternatively, two or more of the blocks of the exemplary method 500 may be performed in parallel.

Exemplary Environment and Exemplary Device

Figure 6:
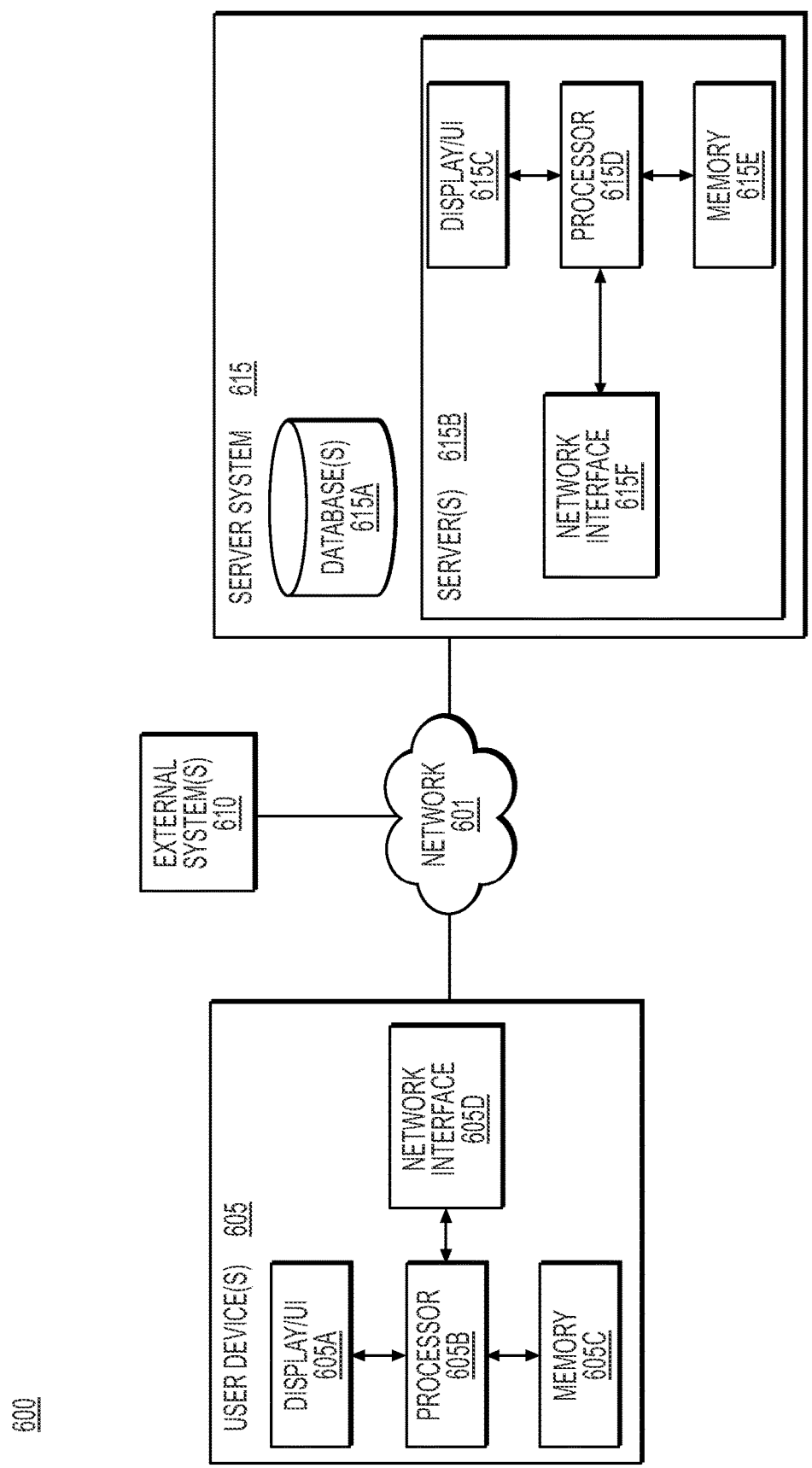
FIG. 6 depicts an exemplary environment that may be utilized with techniques presented herein, according to one or more embodiments.

FIG. 6 depicts an exemplary environment 600 that may be utilized with techniques presented herein. One or more user device(s) 605, one or more external system(s) 610, and one or more server system(s) 615 may communicate across a network 601. As will be discussed in further detail below, one or more server system(s) 615 may communicate with one or more of the other components of the environment 600 across network 601. The one or more user device(s) 605 may be associated with a user.

In some embodiments, the components of the environment 600 are associated with a common entity, e.g., a veterinarian, clinic, animal specialist, research center, or the like. In some embodiments, one or more of the components of the environment is associated with a different entity than another. The systems and devices of the environment 600 may communicate in any arrangement.

The user device 605 may be configured to enable the user to access and/or interact with other systems in the environment 600. For example, the user device 605 may be a computer system such as, for example, a desktop computer, a mobile device, a tablet, etc. In some embodiments, the user device 605 may include one or more electronic application(s), e.g., a program, plugin, browser extension, etc., installed on a memory of the user device 605.

The user device 605 may include a display/user interface (UI) 605A, a processor 605B, a memory 605C, and/or a network interface 605D. The user device 605 may execute, by the processor 605B, an operating system (0/S) and at least one electronic application (each stored in memory 605C). The electronic application may be a desktop program, a browser program, a web client, or a mobile application program (which may also be a browser program in a mobile O/S), an applicant specific program, system control software, system monitoring software, software development tools, or the like. For example, environment 600 may extend information on a web client that may be accessed through a web browser. In some embodiments, the electronic application(s) may be associated with one or more of the other components in the environment 600. The application may manage the memory 605C, such as a database, to transmit streaming data to network 601. The display/UI 605A may be a touch screen or a display with other input systems (e.g., mouse, keyboard, etc.) so that the user(s) may interact with the application and/or the O/S. The network interface 605D may be a TCP/IP network interface for, e.g., Ethernet or wireless communications with the network 601. The processor 605B, while executing the application, may generate data and/or receive user inputs from the display/UI 605A and/or receive/transmit messages to the server system 615, and may further perform one or more operations prior to providing an output to the network 601.

External systems 610 may be, for example, one or more third party and/or auxiliary systems that integrate and/or communicate with the server system 615 in performing various eating detection tasks. External systems 610 may be in communication with other device(s) or system(s) in the environment 600 over the one or more networks 601. For example, external systems 610 may communicate with the server system 615 via API (application programming interface) access over the one or more networks 601, and also communicate with the user device(s) 605 via web browser access over the one or more networks 601.

In various embodiments, the network 601 may be a wide area network ("WAN"), a local area network ("LAN"), a personal area network ("PAN"), or the like. In some embodiments, network 601 includes the Internet, and information and data provided between various systems occurs online. "Online" may mean connecting to or accessing source data or information from a location remote from other devices or networks coupled to the Internet. Alternatively, "online" may refer to connecting or accessing a network (wired or wireless) via a mobile communications network or device. The Internet is a worldwide system of computer networks—a network of networks in which a party at one computer or other device connected to the network can obtain information from any other computer and communicate with parties of other computers or devices. The most widely used part of the Internet is the World Wide Web (often-abbreviated "WWW" or called "the Web"). A "website page" generally encompasses a location, data store, or the like that is, for example, hosted and/or operated by a computer system so as to be accessible online, and that may include data configured to cause a program such as a web browser to perform operations such as send, receive, or process data, generate a visual display and/or an interactive interface, or the like.

The server system 615 may include an electronic data system, e.g., a computer-readable memory such as a hard drive, flash drive, disk, etc. In some embodiments, the server system 615 includes and/or interacts with an application programming interface for exchanging data to other systems, e.g., one or more of the other components of the environment.

The server system 615 may include a database 615A and at least one server 615B. The server system 615 may be a computer, system of computers (e.g., rack server(s)), and/or or a cloud service computer system. The server system may store or have access to database 615A (e.g., hosted on a third party server or in memory 615E). The server(s) may include a display/UI 615C, a processor 615D, a memory 615E, and/or a network interface 615F. The display/UI 615C may be a touch screen or a display with other input systems (e.g., mouse, keyboard, etc.) for an operator of the server 615B to control the functions of the server 615B. The server system 615 may execute, by the processor 615D, an operating system (O/S) and at least one instance of a servlet program (each stored in memory 615E).

Although depicted as separate components in FIG. 6, it should be understood that a component or portion of a component in the environment 600 may, in some embodiments, be integrated with or incorporated into one or more other components. For example, a portion of the display 615C may be integrated into the user device 605 or the like. In some embodiments, operations or aspects of one or more of the components discussed above may be distributed amongst one or more other components. Any suitable arrangement and/or integration of the various systems and devices of the environment 600 may be used.

In the previous and following methods, various acts may be described as performed or executed by a component from FIG. 6, such as the server system 615, the user device 605, or components thereof. However, it should be understood that in various embodiments, various components of the environment 600 discussed above may execute instructions or perform acts including the acts discussed above. An act performed by a device may be considered to be performed by a processor, actuator, or the like associated with that device. Further, it should be understood that in various embodiments, various steps may be added, omitted, and/or rearranged in any suitable manner.

In general, any process or operation discussed in this disclosure that is understood to be computer-implementable, such as the processes illustrated in FIGS. 1-5, may be performed by one or more processors of a computer system, such any of the systems or devices in the environment 600 of FIG. 6, as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices in FIG. 6. One or more processors of a computer system may be included in a single computing device or distributed among a plurality of computing devices. A memory of the computer system may include the respective memory of each computing device of the plurality of computing devices.

Figure 7:
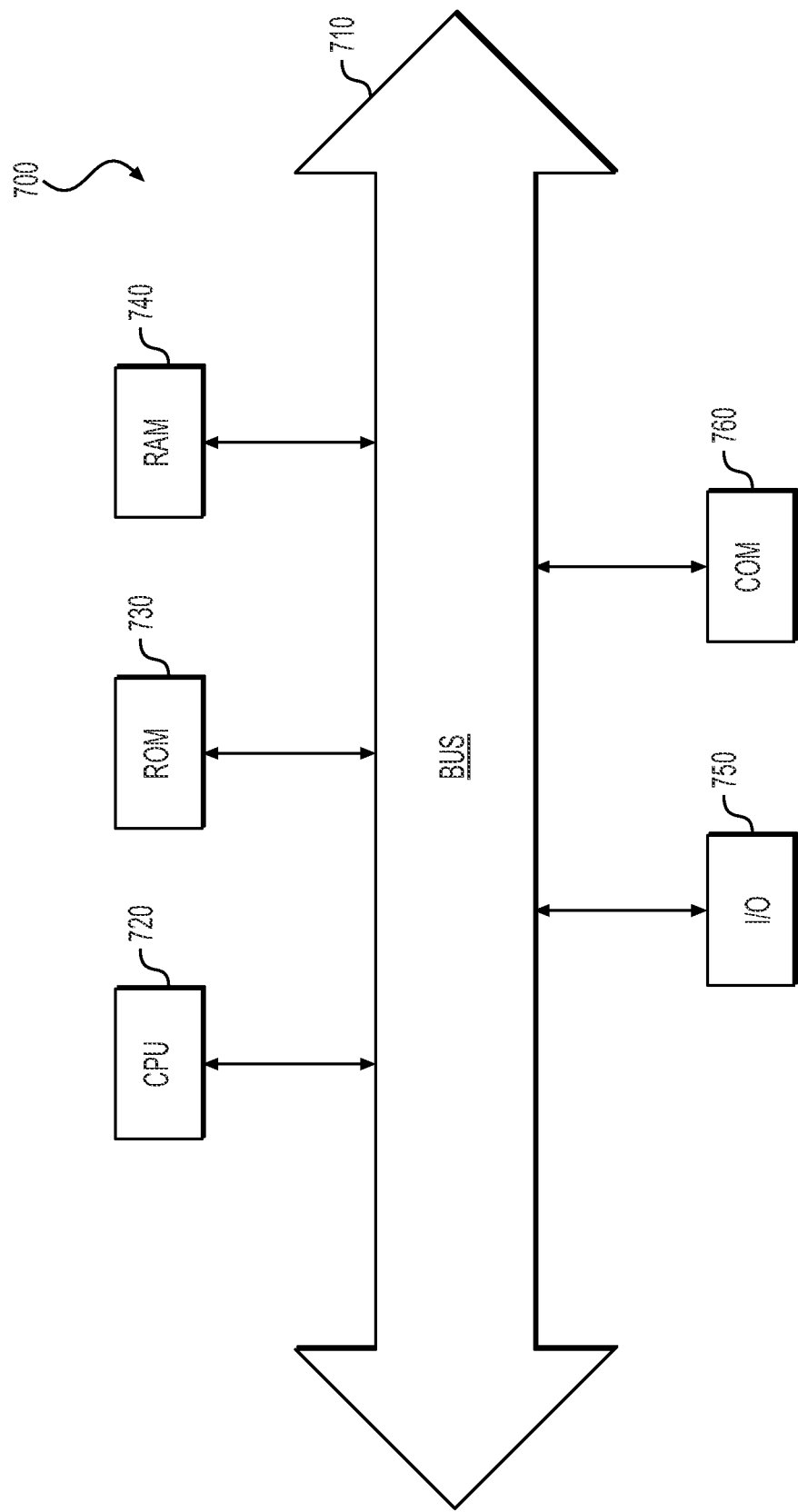
FIG. 7 depicts an example of a computing device that may execute the techniques described herein, according to one or more embodiments.

FIG. 7 is a simplified functional block diagram of a computer 700 that may be configured as a device for executing the environments and/or the methods of FIGS. 1-5, according to exemplary embodiments of the present disclosure. For example, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example, a bus, message queue, network, or multi-core message-passing scheme.

Device 700 also may include a main memory 740, for example, random access memory (RAM), and also may include a secondary memory 730. Secondary memory 730, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage unit may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include other similar means for allowing computer programs or other instructions to be loaded into device 700. Examples of such means may include a program cartridge and cartridge interface (such as that found in video game devices), a removable memory chip (such as an EPROM, or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical, or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems and programming languages of such equipment are conventional in nature, and it is presumed that those skilled in the art are adequately familiar therewith. Device 700 also may include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

Reference to any particular activity is provided in this disclosure only for convenience and not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used above may be interpreted in its broadest reasonable manner, even though it is being used in conjunction with a detailed description of certain specific examples of the present disclosure. Indeed, certain terms may even be emphasized above; however, any terminology intended to be interpreted in any restricted manner will be overtly and specifically defined as such in this Detailed Description section. Both the general description and the detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially" and "generally," are used to indicate a possible variation of ±10% of a stated or understood value.

As used herein, a term such as "user" or the like generally encompasses a pet parent and/or pet parents. A term such as "pet" or the like generally encompasses a user's pet, where the term may encompass multiple pets. A term such as "provider" or the like generally encompasses a pet care business It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for using historical pet eating data to determine changes in pet eating behavior, the method comprising:
    receiving, by one or more processors, pet sensor data captured in real-time by one or more pet sensors worn by a pet, wherein the pet sensor data includes pet eating data corresponding to one or more pet eating events, wherein the pet sensor data includes one or more sensor identifiers corresponding to the one or more pet sensors and one or more time durations that the pet wore the one or more pet sensors;
    analyzing, by the one or more processors, the one or more pet sensors and the one or more time durations to determine a historical sensor wearing ratio;
    updating, by the one or more processors, a plurality of historical pet eating data records in a database to include the pet eating data, wherein each record of the plurality of historical pet eating data records includes a historical meal event value, a corresponding historical meal event date, and the historical sensor wearing ratio;
    determining, by the one or more processors, a subset of the plurality of historical pet eating data records that each include a historical sensor wearing ratio that meets or exceeds a sensor wearing threshold, wherein the determining includes removing at least one of the plurality of historical pet eating data records from the database;
    determining, by the one or more processors, an expected distribution based on the subset of the plurality of historical pet eating data records, the expected distribution including a baseline, an upper threshold, and a lower threshold, wherein the upper threshold and the lower threshold correspond to the baseline;
    receiving, by the one or more processors, current pet data from the one or more pet sensors worn by the pet, the current pet data including a total meal event value;
    analyzing, by the one or more processors, whether the total meal event value exceeds the upper threshold or the lower threshold to determine a result;
    receiving, by the one or more processors, additional pet behavior data for the pet, wherein the additional pet behavior data includes one or more of: scratching data of the pet, licking data of the pet, sleeping data of the pet, and drinking data of the pet;
    calculating, by the one or more processors, a wellness score based on analyzing the additional pet behavior data and the pet sensor data;
    generating, by the one or more processors, a user-interactive graphical display of the wellness score, the result, the current pet data, the expected distribution, the upper threshold, and the lower threshold;
    outputting, by the one or more processors, the user-interactive graphical display on a user interface of a mobile device, wherein the user-interactive graphical display includes an electronic communication option;
    receiving, by the one or more processors, a user selection corresponding to the electronic communication option to send a real-time communication to an external server system; and
    in response to the user selection, transmitting, by the one or more processors, an electronic communication that includes the user-interactive graphical display from the mobile device via a network to the external server system.

2. The computer-implemented method of claim 1, wherein the baseline is determined based on the subset of the plurality of historical pet eating data records that do not include one or more outliers.

3. The computer-implemented method of claim 2, wherein the upper threshold and the lower threshold are determined based on at least one standard deviation from the baseline.

4. The computer-implemented method of claim 1, further comprising:
    determining, by the one or more processors, one or more historical pet eating data records, of the plurality of historical pet eating data records, that are each indicative of an outlier; and
    excluding, by the one or more processors, any of the one or more historical pet eating data records that are each indicative of an outlier from the subset of the plurality of historical pet eating data records.

5. The computer-implemented method of claim 1, wherein determining the subset of the plurality of historical pet eating data records further comprises:
    removing from the database, by the one or more processors, a remaining one or more of the plurality of historical pet eating data records that each include a historical sensor wearing ratio less than the sensor wearing threshold.

6. The computer-implemented method of claim 1, wherein determining the subset of the plurality of historical pet eating data records further comprises:
    determining, by the one or more processors, one or more historical pet eating data records, of the plurality of historical pet eating data records, that are each indicative of an outlier;
    excluding, by the one or more processors, the one or more historical pet eating data records that are indicative of an outlier from the plurality of historical pet eating data records; and
    determining, by the one or more processors, the subset of the plurality of historical pet eating data records from a remaining one or more historical pet eating data records, of the plurality of historical pet eating data records.

7. The computer-implemented method of claim 1, wherein the current pet data includes a pet identifier, a corresponding date, and a sensor wearing ratio indicating a time ratio that the pet wore the pet sensor on the corresponding date.

8. The computer-implemented method of claim 7, wherein the total meal event value includes a sum of a duration of all meal events that occurred on the corresponding date.

9. The computer-implemented method of claim 8, wherein the total meal event value is measured in seconds, minutes, or hours.

10. The computer-implemented method of claim 1, wherein the graphical display includes at least one of: an eating above average notification, an eating average notification, or an eating below average notification.

11. The computer-implemented method of claim 1, wherein the baseline is determined to be valid when the subset of the plurality of historical pet eating data records comprises a predetermined number of historical pet eating data records, wherein each of the predetermined number of historical pet eating data records is associated with a historical meal event date within a predetermined time range.

12. The computer-implemented method of claim 11, wherein each of the predetermined number of historical pet eating data records is further associated with a historical sensor wearing ratio meeting or exceeding a baseline sensor wearing threshold.

13. The computer-implemented method of claim 1, the method further comprising:
    determining, by the one or more processors, a baseline that includes a total meal event length, wherein the baseline is based on the subset of the plurality of historical pet eating data records;
    analyzing, by the one or more processors, the baseline to determine whether the baseline is valid; and
    in response to determining that the baseline is valid, outputting, by the one or more processors, the baseline to the user interface of the mobile device.

14. A computer system for using historical companion pet eating data to determine changes in companion pet eating behavior, the computer system comprising:
    at least one memory storing instructions; and
    at least one processor configured to execute the instructions to perform operations comprising:
        receiving pet sensor data captured in real-time by one or more pet sensors worn by a pet, wherein the pet sensor data includes pet eating data corresponding to one or more pet eating events, wherein the pet sensor data includes one or more sensor identifiers corresponding to the one or more pet sensors and one or more time durations that the pet wore the one or more pet sensors;
        analyzing the one or more pet sensors and the one or more time durations to determine a historical sensor wearing ratio;
        updating a plurality of historical pet eating data records in a database to include the pet eating data, wherein each record of the plurality of historical pet eating data records includes a historical meal event value, a corresponding historical meal event date, and the historical sensor wearing ratio;
        determining a subset of the plurality of historical pet eating data records that each include a historical sensor wearing ratio that meets or exceeds a sensor wearing threshold, wherein the determining includes removing at least one of the plurality of historical pet eating data records from the database;
        determining an expected distribution based on the subset of the plurality of historical pet eating data records, the expected distribution including a baseline, an upper threshold, and a lower threshold, wherein the upper threshold and the lower threshold correspond to the baseline;
        receiving current pet data from the one or more pet sensors, the current pet data including a total meal event value;
        analyzing whether the total meal event value exceeds the upper threshold or the lower threshold to determine a result;
        receiving additional pet behavior data for the pet, wherein the additional pet behavior data includes one or more of: scratching data of the pet, licking data of the pet, sleeping data of the pet, and drinking data of the pet;
        calculating a wellness score based on analyzing the additional pet behavior data and the pet sensor data;
        generating a user-interactive graphical display of the wellness score, the result, the current pet data, the expected distribution, the upper threshold, and the lower threshold;
        outputting the user-interactive graphical display on a user interface of a mobile device, wherein the user-interactive graphical display includes an electronic communication option;
        receiving a user selection corresponding to the electronic communication option to send a real-time communication to an external server system; and
        in response to the user selection, transmitting an electronic communication that includes the user-interactive graphical display from the mobile device via a network to the external server system.

15. The computer system of claim 14, wherein the baseline is determined based on the subset of the plurality of historical pet eating data records that do not include one or more outliers.

16. The computer system of claim 15, wherein the upper threshold and the lower threshold are determined based on at least one standard deviation from the baseline.

17. The computer system of claim 14, the operations further comprising:
    determining one or more historical pet eating data records, of the plurality of historical pet eating data records, that are each indicative of an outlier; and
    excluding any of the one or more historical pet eating data records that are each indicative of an outlier from the subset of the plurality of historical pet eating data records.

18. The computer system of claim 14, wherein determining the subset of the plurality of historical pet eating data records further comprises:
    removing, from the database, a remaining one or more of the plurality of historical pet eating data records that each include a historical sensor wearing ratio less than the sensor wearing threshold.

19. A non-transitory computer-readable medium containing instructions that, when executed by a processor, cause the processor to perform operations for using historical companion pet eating data to determine changes in companion pet eating behavior, the operations comprising:
    receiving pet sensor data captured in real-time by one or more pet sensors worn by a pet, wherein the pet sensor data includes pet eating data corresponding to one or more pet eating events, wherein the pet sensor data includes one or more sensor identifiers corresponding to the one or more pet sensors and one or more time durations that the pet wore the one or more pet sensors;

analyzing the one or more pet sensors and the one or more time durations to determine a historical sensor wearing ratio;

updating a plurality of historical pet eating data records in a database to include the pet eating data, wherein each record of the plurality of historical pet eating data records includes a historical meal event value, a corresponding historical meal event date, and the historical sensor wearing ratio;

determining a subset of the plurality of historical pet eating data records that each include a historical sensor wearing ratio that meets or exceeds a sensor wearing threshold, wherein the determining includes removing at least one of the plurality of historical pet eating data records from the database;

determining an expected distribution based on the subset of the plurality of historical pet eating data records, the expected distribution including a baseline, an upper threshold, and a lower threshold, wherein the upper threshold and the lower threshold correspond to the baseline;

receiving current pet data from the one or more pet sensors, the current pet data including a total meal event value;

analyzing whether the total meal event value exceeds the upper threshold or the lower threshold to determine a result;

receiving additional pet behavior data for the pet, wherein the additional pet behavior data includes one or more of scratching data of the pet, licking data of the pet, sleeping data of the pet, and drinking data of the pet;

calculating a wellness score based on analyzing the additional pet behavior data and the pet sensor data;

generating a user-interactive graphical display of the wellness score, the result, the current pet data, the expected distribution, the upper threshold, and the lower threshold;

outputting the user-interactive graphical display on a user interface of a mobile device, wherein the user-interactive graphical display includes an electronic communication option;

receiving a user selection corresponding to the electronic communication option to send a real-time communication to an external server system; and in response to the user selection, transmitting an electronic communication that includes the user-interactive graphical display from the mobile device via a network to the external server system.

20. The non-transitory computer-readable medium of claim 19, wherein the current pet data includes a pet identifier, a corresponding date, and a sensor wearing ratio indicating a time ratio that the pet wore the pet sensor on the corresponding date.

* * * * *